United States Patent [19]

Kumar

[11] Patent Number: 5,770,370
[45] Date of Patent: Jun. 23, 1998

[54] NUCLEASE PROTECTION ASSAYS

[75] Inventor: Rajan Kumar, Robbinsville, N.J.

[73] Assignee: David Sarnoff Research Center, Inc., Princeton, N.J.

[21] Appl. No.: 665,104

[22] Filed: Jun. 14, 1996

[51] Int. Cl.$^6$ .............................. C12Q 1/68; C12P 19/34; C07H 21/02; C07H 21/04

[52] U.S. Cl. .......................... 435/6; 435/91.1; 435/91.2; 435/196; 435/199; 436/501; 536/23.1; 536/24.1; 536/24.3; 536/24.31; 536/24.32; 536/24.33; 935/78

[58] Field of Search .............................. 435/6, 91.1, 91.2, 435/196, 199; 436/501; 536/23.1, 24.1, 24.3, 24.31, 24.32, 24.33; 935/78

[56] References Cited

U.S. PATENT DOCUMENTS

| | | | |
|---|---|---|---|
| 4,946,773 | 8/1990 | Maniatis et al. | 435/6 |
| 5,143,854 | 9/1992 | Pirrung et al. | 435/518 |
| 5,359,115 | 10/1994 | Cambell et al. | 558/110 |
| 5,420,328 | 5/1995 | Campbell | 558/110 |
| 5,424,186 | 6/1995 | Fodor et al. | 435/6 |
| 5,445,934 | 8/1995 | Fodor et al. | 435/6 |

FOREIGN PATENT DOCUMENTS

| | | |
|---|---|---|
| WO 92/10092 | 6/1992 | WIPO . |
| WO 93/06121 | 4/1993 | WIPO . |

OTHER PUBLICATIONS

Matthews et al., Analytical Biochemistry 169:1–25, Feb. 1988.

Landgraf et al., Analytical Biochemistry 198:86–91, 1991.

Goodchild, Bioconjugate Chemistry 1(3):165–187, 1990.

Ausubel et al., Short Protocols In Molecular Biology, John Wiley & Sons, Unit 6.4, pp. 6–7 to 6–10, and Units 4.6–4.7, pp. 4–14 to 4–20, 1992.

Walmsely and Patient, *Mol. Biotechnol.*, vol. 1, pp. 265–275 (1994).

Lau et al., *Anal. Biochem.*, vol. 209, pp. 360–366 (1993).

Haines and Gillispie, *Biotechniques*, vol. 12, pp. 736–741 (1992).

Strauss and Jacobowitz, *Brain Res. Mol. Brain Res.*, vol. 20, pp. 229–239 (1993).

*Primary Examiner*—Stephanie W. Zitomer
*Assistant Examiner*—Paul B. Tran
*Attorney, Agent, or Firm*—William J. Burke

[57] ABSTRACT

The invention provides nuclease protection assay comprising: (A) attaching a nucleic acid probe comprising a first nucleotide sequence to a solid surface area; (B) contacting the nucleic acid probe with a nucleic acid template under conditions that promote hybridization between complementary polynucleotides, forming a probe-template complex if the template includes a segment that is complementary to the probe; (C) contacting the probe-template complex with a nuclease effective to selectively cleave the nucleotide bonds of (1) the first nucleotide sequence when the first nucleotide sequence is single stranded or (2) mismatched regions of the first nucleotide sequence when the first nucleotide sequence is in duplex nucleic acid; and (D) detecting the presence of duplex nucleic acids formed by the probe and template nucleic acids by detecting the presence of the first nucleotide sequence.

19 Claims, 2 Drawing Sheets

FIG. 1

FIG. 2A  10,000 PROBES/PLATE; 120,000 DIFFERENT PROBES ON 12 PLATES

FIG. 2B  A SIX-SIDED HYBRIDIZATION CYLINDER

NUCLEASE PROTECTION ASSAYS

This invention was made with U.S. Government support under Contract No. 70NANB5H1037. The U.S. Government has certain rights in this invention.

This patent application is being concurrently filed with the following related U.S. patent applications: "Method for Polynucleotide Sequencing", Ser. No. 08/665,210; "Microfluidic for Nucleic Acid Amplification", Ser. No. 08/665,209; "Method for Amplifying a Polynucleotide", Ser. No. 08/663,688; "Automated Nucleic Acid Amplification", Ser. No. 08/664,780; and "Padlock Probe Detection", Ser. No. 08/665,208; all of which filed Jun. 14, 1996. This patent application is related to the following copending U.S. patent applications: "Assay System", Ser. No. 60/009,517, filed Nov. 3, 1995; "Magnet", Ser. No. 60/006,202, filed Nov. 3, 1995; and "Parallel Reaction Cassette and Associated Devices", Ser. No. 60/010,513, filed Jan. 24, 1996.

The invention relates to methods of conducting nuclease protection assays by measuring the extent to which a label is released from a solid support as a result of contacting the nuclease.

Nuclease protection has provided a sensitive method for determining whether a nucleic acid sample contains a specific sequence or determining the amount of a sequence in a sample. The assay is conducted by first co-incubating a sample nucleic acid with a nucleic acid probe under suitable hybridization conditions, followed by exposing the co-incubated nucleic acids to a nuclease that hydrolyses any portion of the nucleic acid probe that is single-stranded. If the sample has in sufficient amount a polynucleotide sequence complementary to the nucleic acid probe, then the probe is protected from digestion through forming a nuclease-protected duplex structure with the complementary sequence. Typically the assay has been conducted in solution phase and the post-assay analysis has required an electrophoretic step used to identify whether nucleic acid probe of the appropriate size has been protected.

In a preferred embodiment, the present invention simplifies the detection step to a straight-forward step of detecting whether a label remains on a defined surface. Thus, detecting the outcome of the assay can be as simple as whether a color or fluorescence remains attached to a defined surface.

SUMMARY OF THE INVENTION

The invention provides nuclease protection assay comprising: (A) attaching a nucleic acid probe comprising a first nucleotide sequence to a solid surface area; (B) contacting the nucleic acid probe with a nucleic acid template under conditions that promote hybridization between complementary polynucleotides, forming a probe-template complex if the template includes a segment that is complementary to the probe; (C) contacting the probe-template complex with a nuclease effective to selectively cleave the nucleotide bonds of (1) the first nucleotide sequence when the first nucleotide sequence is single stranded or (2) mismatched regions of the first nucleotide sequence when the first nucleotide sequence is in duplex nucleic acid; and (D) detecting the presence of duplex nucleic acids formed by the probe and template nucleic acids by detecting the presence of the first nucleotide sequence. In one embodiment, the attaching step occurs prior to the first contacting step. In one embodiment, the attaching comprises synthesizing the nucleic acid probe on the solid surface area. In one embodiment, the probe is attached to the solid surface area subsequent to hybridization between the probe and a template DNA. Preferably, the solid surface area comprises plastic, glass, cellulose or a cellulose derivative, nylon or other synthetic membranous material, or ceramic. In one embodiment, the solid surface area is a microparticle, which is preferably paramagnetic.

In one embodiment, the attaching step occurs prior to the first contacting step, and a single solid surface is formed into a cylinder or a multiplicity of such solid surfaces are joined and formed into a cylinder, with the attached probe on the interior or exterior surface of the cylinder. In this embodiment, the assay further comprises rotating the cylinder to permit all surfaces containing the attached probe to come into contact with the template and nuclease. Preferably, the nuclease used in the assay is S1 nuclease, mung bean nuclease, ribonuclease A, ribonuclease T1, exonuclease VII, Bal 31, micrococcal nuclease, neurospora endonuclease or nuclease P1. Preferably, step (C) further comprises washing unhybridized DNA template from the probe-template complex. The nuclease can contact the probe-template complex before or after the unhybridized DNA template is washed from the probe-template complex. Preferably, the nucleic acid probe comprises one or more dinucleotides whose intranucleotide linkages are resistant to the nuclease in use or the nucleic acid probe is attached to the solid surface area by a linkage that is resistant to the nuclease in use. Preferably, the one or more nuclease resistant linkages are located at or proximate to one or both of the termini of the probe. Preferably, nuclease resistant linkages are located at a terminus of the probe that is attached to the solid surface area. In one embodiment, the nucleic acid probe has a linker tail at one end, which linker tail can comprise a second nucleotide sequence that is not required to participate in the hybridization reaction and that is resistant to digestion by the nuclease whether or not it is hybridized with another polynucleotide.

The nuclease resistant linkages preferably comprise (a) analogs of the phosphodiester intranucleotide linkage where one or more of the carbon-bonded oxygens are replaced with amino, hydrocarbylamino or sulfur, (b) a linkage between ribosides of the linked nucleotides wherein at least one said riboside is a 2'-deoxyriboside and the nuclease is a ribonuclease, (c) a linkage between ribosides of the linked nucleotides wherein at least one said riboside is a 2'-hydrocarbyl-riboside (d) a protein nucleic acid backbone, or (e) the backbone of a phosphothioxate nucleotide, a phosphorothioate nucleotide phosphomorpholidate nucleotide, or a methylphosphonate nucleotide. For the purposes of this application a hydrocarbyl substituent is a aliphatic hydrocarbon, preferably having from 1 to 6 carbons.

Preferably, the nucleic acid probe comprises a label, and the label is releasable from the nucleic acid probe when any nucleotide bond of the first nucleotide sequence is cleaved. The label can be a radioisotope, a fluorescent or light-absorbing dye, a signal-generating enzyme or a member of a binding pair. Preferably, the label is attached to a nucleotide of the nucleic acid probe that is linked to another nucleotide of the nucleic acid probe by a nuclease resistant linkage. The nucleic acid probe can comprise a member of a binding pair. Preferably, the member of the binding pair is one of (a) the biotin/streptavidin binding pair, (b) an antigen/antibody specific for the antigen binding pair, (c) the amine/hydrazine moiety binding pair, or (d) the Protein A/immunoglobulinG binding pair. Preferably, the member of the binding pair is attached to a nucleotide of the nucleic acid probe that is linked to another nucleotide of the nucleic acid probe by a nuclease resistant linkage. In one embodiment, the attaching step of the assay comprises, after the first contacting step, contacting the nucleic acid probe with the solid surface area, where the other member of the binding pair is bonded to the solid surface area and functions to bond and attach the nucleic acid probe.

The assay can be conducted with several separate solid surfaces having distinct nucleic acid probes such that the solid surfaces can comprise on a first solid surface to which a first nucleic acid probe attached and on a second, distinct surface to which a second nucleic acid probe is attached. These first and second surfaces are both processed through the assay steps. In one embodiment, the first nucleic acid probe and the second nucleic acid probe both comprise a label, which may be the same or different, with each label releasable from its nucleic acid probe when any nucleotide bond of its first nucleotide sequence is cleaved, and with the amount of label attached to the first nucleic acid probe differing from the amount attached to the second label, with the amount of label approximately in inverse proportion to the anticipated frequency of the template polynucleotide that binds to the respective first or second nucleic acid probe.

The assay can be used for the identification or quantitation of an expressed mRNA. In this application, preferably the nucleic acid probe comprises at its 3' end a polyT segment and the first polynucleotide sequence comprises at least about 10 nucleotides distinct from the polyT segment, with the polyT-containing nucleic acid probe being complementary to the mRNA.

The invention also provides an apparatus for conducting nuclease protection assays comprising a chamber having a liquid fill volume, a rotation device for rotating a cylinder of material on which one or more nucleic acid probes are attached on the inner or outer cylinder surface such that through each rotation of the cylinder all of the probe-attached surfaces of the cylinder intersect the liquid fill volume, and a temperature control device for maintaining the chamber at a temperature.

The assay of the invention, together with all its preferred and alternate embodiments, can be used as the basis for a method for the sequencing of a sample polynucleotide, the method comprising: (A) preparing an array having a multitude of distinct nucleic acid probes, each of known nucleotide sequence, each comprising a first polynucleotide sequence, and each immobilized at a separate, identifiable solid surface area in the array, with each immobilized nucleic acid probe comprising a label attached to the nucleic acid probe, which label is releasable from the nucleic acid probe when any nucleotide bond of the first polynucleotide sequence of the attached nucleic acid probe is cleaved; (B) contacting the array with the sample polynucleotide or fragments thereof under conditions that promote hybridization between complementary nucleic acids; (C) contacting the solid surface areas of the array with a nuclease effective to selectively cleave the nucleotide bonds of (1) a first polynucleotide sequences when such a first polynucleotide sequence is single stranded or (2) mismatched regions of a first polynucleotide sequence when such a first polynucleotide sequence is in duplex nucleic acid; (D) removing released label from the solid surface areas; and (E) detecting any label remaining on the solid surface areas and identifying the nucleic acid probe immobilized at the solid surface areas where label is detected. The sequencing method can further comprise: (F) compiling the sub-sequences of the sample polynucleotide identified through their protection from nuclease digestion, which protection results in the detection of label at the solid surface area of a complementary first polynucleotide sequence; and (G) aligning the detected sequences by identifying sequence overlaps between the compiled sub-sequences. The steps F and G are done manually or by computer. In this method, preferably, the first polynucleotide sequences of the nucleic acid probes comprise at least about 8-mers. Preferably, the first nucleotide sequences are 8-mers and the array comprises first polynucleotide sequences for each of the 65,536 possible such sequences or multiple arrays are processed which together comprise first polynucleotide sequences for each of the 65,536 possible such sequences.

DEFINITIONS

The following terms shall have the meaning set forth below:

label is releasable from the nucleic acid probe

A label is releasable from the nucleic acid probe if, after the nuclease contacting step of the invention, the label can be washed away without a hydrolytic step or, where the nucleic acid probe is attached to the solid surface by a binding pair, the label can be washed away without disrupting the binding pair interaction.

microparticles

A microparticle can have any shape, and preferably is spherical. Preferably, it has a diameter of 1 mm or less, and more preferably, 500 microns or less. In certain preferred embodiments, the microparticles have a diameter from about 0.5 micron to about 25 microns, and more preferably about 1 micron to about 5 microns, and even more preferably, about 2 microns to about 4 microns. Microparticles are comprised of any suitable material, the choice of material being guided by its characteristics, which preferably include minimal non-specific absorptive characteristics, such as that of polystyrene. In other embodiments, the microparticles are comprised of, for example, plastic, glass, cellulose, a cellulose derivative, nylon, polytetrafluoroethylene ("TEFLON"), ceramic and the like. A paramagnetic bead can be comprised of, for example, iron dispersed in a polystyrene matrix. Such beads can be obtained, for example, from Dynal (Oslo, Norway), which markets such beads with conjugated biomolecules, and Bang Laboratories, (Carmel, Ind.).

nucleotide bond of the first nucleotide sequence

A "nucleotide bond of the first nucleotide sequence" is any nucleotide bond to the 5' or 3' side of a nucleotide in the first nucleotide sequence, where a "nucleotide bond" is one or the other of the esters of a phosphodiester linkage or an analog thereof that is cleavable with a nuclease utilized in the assay of the invention.

nucleotide sequence or polynucleotide

For the purposes of this application, a nucleotide sequence or polynucleotide comprises purine or pyrimidine bases, or analogs thereof, arranged in a polymer with the appropriate spacing for base-pairing with a complementary oligonucleotide that has the riboside-phosphodiester linkage utilized in nature.

nuclease-resistant linkage

A nuclease resistant linkage is a linkage between the purine or pyrimidine bases or analogs thereof of a nucleotide sequence that is resistant to cleavage by the particular nuclease to be used in the assay. In some cases, the linkage includes the typical phosphodiester bridge found in natural nucleotide sequences, but is resistant to cleavage because of an adjoining structure such as the presence of a 2'-hydroxyl when the nuclease is a ribonuclease.

selectively cleave

Single-stranded elements of a nucleotide sequence (including mismatched portions of duplex nucleic acid) are "selectively" cleaved if base-paired duplex nucleic acid is not cleaved to any extent that would interfere with the nuclease protection assay functioning to either determine whether nucleotide sequences present in a sample or, in some cases, quantitate the amount of such a nucleotide sequence in the sample.

DETAILED DESCRIPTION

The present invention provides a method of testing whether a sample nucleic acid hybridizes with and protects from a nuclease a nucleic acid probe that is bound to a solid surface. The sample nucleic acid is termed a "template" herein to facilitate distinguishing this nucleic acid from the nucleic acid probe. The hybridization can occur in the solution phase if the nucleic acid probe has a suitable binding pair bonded to it that allows it to be attached to the solid surface prior to the nuclease treatment step. The nucleic acid probe preferably has a label that remains bound to the solid surface if a nucleic acid template has protected the nucleic acid probe from cleavage, but is released from the solid support if the nucleic acid probe is cleaved. In this way, nuclease protection is simply indicated by the presence of label, such as a fluorescent label, on the solid surface. Alternatively, after the nuclease protection phase of the assay, protected label can then be removed from the solid surface and quantitated in the solution phase. For example, the protecting nucleic acid template can be removed, for instance with heat denaturation, and the label removed with another nuclease treatment.

The present invention relates to a method for the detection of a polynucleotide in a mixture of polynucleotides, such as the amplification products of a nucleic acid amplification procedure or a solution of nucleic acid isolated from a biological source. This method is used in the context of benchtop laboratory research, as well as in the conduct of large-scale screening of clinical or forensic samples for the analysis diseases or conditions, or for the analysis of evidence taken from a crime scene. Importantly, this detection method can be used in the context of a microfluidics-based device for automatedly moving fluids in and out of a reaction chamber, which has been disclosed in U.S. patent Ser. No. 60/010,513, entitled "Parallel Reaction Cassette and Associated Devices," filed Jan. 24, 1996, Attorney Docket No. 1 1895, the contents of which are incorporated herein by reference, and in the context of other procedures that accomodate the analysis and detection of single or multiple polynucleotides of interest.

Hybridization conditions for use in the nuclease protection methods of the invention can be selected based on the description in Ausubel et al., *Short Protocols in Molecular Biology,* John Wiley & Sons, New York, 1992, Unit 6.4, page 6-7 to page 6-10. Hybridization conditions are also described in Ausubel et al., *Current Protocols in Molecular Biology,* John Wiley & Sons, New York, as updated as of June, 1996 and Sambrook et al., *DNA Cloning, A Laboratory Manual,* Cold Spring Harbor, 1989 (these texts collectively referred to as "Ausubel et al. and Sambrook et al."). Hybridization conditions are also described in *Hybridization with Nucleic Acid Probes,* Part I and Part II, Elsevier, New York and in "Molecular Biology Protocols," web-site: listeria.nwfsc.noaa.gov/protocols.html.

Typically, prior to the hybridization step the nucleic acid template is denatured to increase the amount of nucleotide sequence that is not involved in a base-pairing interactions, which interactions would decrease hybridization with the nucleic acid probe.

As will be recognized, the temperature of hybridization will depend on the G/C content of the nucleic acid probe, the length of the nucleic acid probe and the hybridization solution. Discussions of these temperature variables can be found in Ausubel et al., pi Short Protocols in Molecular Biology,John Wiley & Sons, New York, 1992, Unit 6.4, page 6-7 to page 6-10 and in *Hybridization with Nucleic Acid Probes,* Part I and Part II, Elsevier, New York.

For use in screening ribonucleic acid, nuclease protection conditions are described in Ausubel et al., *Short Protocols in Molecular Biology,* John Wiley & Sons, New York, 1992, Units 4.6–4.7, page 4-14 to page 4-20. Additional practical guidance on nuclease protection can be found, for example, in 1996 Catalog, Ambion, Inc., Austin, Tex., pages 7–21; Walmsely and Patient, "Quantitative and Qualitative Analysis of Exogenous Gene Expression by S1 Nuclease Protection Assay," *Mol. Biotechnol.* 1: 265–275, 1994; Lau et al., "Critical Assessment of the RNase Protection Assay as a Means of Determining Exon Sizes," *Anal. Biochem.* 209: 360–366, 1993; Haines and Gillispie, "RNA Abundance Measured by a Lysate RNase Protection Assay," *Biotechniques* 12: 736–741, 1992; and Strauss and Jacobowitz, "Quantitative Measurement of Calretinin and Beta-Actin mRNA," *Brain Res. Mol. Brain Res.* 20: 229–239, 1993.

The solid surfaces used in the invention can, for example, be on particles such as beads, can include pores such as are found on many beads used in chemistry, or can be found in the wells of a multi-well plate. Where separate solid surfaces are identified herein, these separate solid surfaces can be adjacent areas of a larger surface, such as separate areas on a flat surface.

In many of the applications of the methods described herein, it is useful to have an array having unique nucleic acid probes at each of a multitude of separate locations. One way to form such an array is to manufacture the nucleic acid probes using the liquid distribution system described by Zanzucchi et al. in "Liquid Distribution System," PCT/US95/14590, a PCT application filed Nov. 9, 1995, Attorney Docket No. 11402G-WO. That liquid distribution system can conduct distinct synthesis in a great number of separate reaction wells, such as 10,000 reaction wells. The synthesis in each reaction well can occur on a bead or microparticle or can occur on the surfaces of the wells, where these surfaces have been appropriately treated. The wells are formed on a plate that is separable from the portions of the liquid distribution system used to shuttle reactive reagents to a multitude of reaction wells. Accordingly, the device can be used to synthesize separate oligonucleotides bound to the solid support in each of the reaction wells. The plate can then be subjected to the nuclease protection methodology described herein. This PCT/US95/14590 patent application and corresponding U.S. application Ser. No. 08/556,036, filed Nov. 9, 1995, Attorney Docket No. 11402G, are incorporated herein in their entirety by reference.

Another way of forming an array having distinct nucleic acid probes at a multitude of distinct sites is to apply the photolithographic synthesis procedures described in a number of patents and patent applications owned by Affymax, Inc. These include Fodor et al., "Very Large Scale Immobilized Polymer Synthesis," W092/10092; Dovor et al., "Method of Synthesizing Diverse Collections of Oligomers," W093/06121; Campbell et al., "Methods for Synthesis of Phosphonate Esters," U.S. Pat. No. 5,359,115; Campbell, "Methods for Synthesis of Phosphonate Esters," U.S. Pat. No. 5,420,328; Fodor et al., "Very Large Scale Immobilized Polymer Synthesis," U.S. Pat. No. 5,424,186; and Pirrung et al., "Large Scale Photolithographic Solid Phase Synthesis of Polypeptides and Receptor Binding Screening Thereof," U.S. Pat. No. 5,143,854.

Of course, the array can be simply constructed by spotting the nucleic acid probes onto an appropriate adsorptive surface such as a nylon filter, a nitrocellulose filter, polycarbonate, polystyrene or another plastic. Alternatively, the array can be constructed on commercial arrays having reactive surfaces to which nucleic acid probes can be covalently coupled. For example, Nunc, (Naperville, Ill.) sells an array with surfaces having covalently attached amine groups (CovaLink NH modules) to which nucleic acid probes can be coupled using water soluble carbodiimides such as 1-ethyl-3-(3-dimethylaminopropyl)-carbodiimide as the condensation reagent.

Methods of synthesizing nucleic acid probes are well known in the art. Such methods are reviewed for example in Caruthers, *Science* 230: 281–285, 1985; Itakura et al., *Ann. Rev. Biochem.* 53: 323–356; Hunkapillar et al., *Nature* 310: 105–110, 1984; and in "Synthesis of Oligonucleotide Derivatives in *Design and Targeted Reaction of Oligonucleotide Derivatives,* CRC Press, Boca Raton, Fla., pages 100 et seq. The phosphoramidite and phosphite triester approaches are most broadly used, but other approaches include the phosphodiester approach, the phosphotriester approach and the H-phosphonate approach.

Methods of attaching labels (i.e., reporter molecules) to polynucleotides are also well known in the art. For instance, Biosearch Products of PerSeptive Biosystems (Framingham, Mass.) markets 5' linker groups that are compatible with phosphoramidite chemistry. One of these groups includes a six-carbon spacer and a terminal amine that is protected with a trifluoroacetyl ("TFAc"). The TFAc protecting group is base-label and is removed during the normal post-synthesis workup of an oligonucleotide synthesized by the phosphoramidite method, which workup involves hydrolysis in the presence of ammonium hydroxide. Another amine-containing linker from this company also has a six-carbon spacer group and has the amine protected with a methoxytrityl ("MMT") group. The MMT group is acid-label, requires a separate deprotection step. Both of these amine linkers can be used to attach molecules such as biotin or fluorescein. These amine spacer groups can also be used to attach other molecules having a free acid that can be used to form an amide with the amine group through a condensation reaction. Another linker from Biosearch Products has a six-carbon spacer with a thiol group protected by a trityl group. The trityl protecting group is removed by treatment with silver nitrate and dithiothreitol. This linker can be used to attach enzymes and molecules that incorporate maleimide. Methods to couple multiple labels can include the attachment of a polymer having a number of reactive sites, such as a number of amino or thiol groups, which reactive sites can be used to attach label. Labelling methods are described in: Sinha and Striepeke, "Oligonucleotides with Reporter Groups Attached to the 5' Terminus" in Oligonucleotides and Analogues: A Practical Approach, Eckstein, Ed., IRL, Oxford, 1991, p. 185 et seq.; Sinha and Cook, "The Preparation and Application of Functionalized Synthetic Oligonucleotides: 3. Use of H-Phosphate Derivatives of Protected Amino-Hexanol and Mercapto-Propanol or Mercapto-Hexanol," Nucleic Acids Research, 1988, Vol. 16, p. 2659 et seq.; Haugland, Molecular Probes Handbook of Fluorescent Probes and Research Chemicals, Molecular Probes, Inc., Eugene, Oreg., 1992, p. 20 et seq.; Theisen et al., "Fluorescent Dye Phosphoramidite Labelling of Oligonucleotides," Tetrahedron Letters, 1992, Vol. 33, p. 3036 et seq.; Rosenthal and Jones, "Genomic Walking and Sequencing by Oligocassette Mediated Polymerase Chain Reaction," Nucleic Acids Research, 1990, Vol. 18, p. 3095 et seq.; Smith et al., "The Synthesis of Oligonucleotides containing an Aliphatic Amino Group at the 5' Terminus—Synthesis of Fluorescent DNA Primers for Use in DNA-Sequence Analysis," Nucleic Acids Research, 1985, Vol. 13, 2399 et seq.

Of course, one of the more common methods of labeling nucleic acid probes is to incorporate $^{32}P$ into the phosphodiester linkage that typically links nucleotides or to incorporate $^3H$ or $^{13}C$ into one of the bases of one of the nucleotides. Additional labeling strategies can take advantage of other physico-chemical properties such as an identifiable nuclear magnetic resonance or electron-spin resonance signal.

The labels in nucleic acid probes are preferably located near the terminus of the probe that is not bound to the solid surface. This helps assure that should any part of the nucleic acid probe be cleaved during the nuclease protection portion of the assay, the label will be separated from the solid support after the solid surface has been appropriately washed. However, the location of the label can be at any position where it will be reproducibly removable from the attachment to the solid support should any part of its first nucleotide sequence be cleaved during the nuclease protection assay. Depending on the particular nucleic acid probe, this labelling position can be adjusted if cleavages that are not effective alone to separate the label from the support nonetheless sufficiently destabilize any duplex formation with the nucleic acid template such that a further cleavages by the nuclease occur and thereby separate the label from the support.

Suitable labels provide sufficient signal over noise ratios, for example, when less than about 100 copies of a target nucleic acid are present per microliter in a sampling; such suitable labels include a radioisotope, a fluorescent dye, or a signal-generating enzyme or a member of a binding pair that can be used to attach a detectable moiety during the detection phase of the assay. Suitable radioisotopes include, but are not limited to, $^3H$, $^{14}C$, and 32P. Suitable fluorescent dyes include, but are not limited to, fluorescein, rhodamine, 7-amino-4-methylcoumarin, dansyl chloride, Cy3, Hoechst 33258, R-phycoerythrin, Quantum Red™, Texas Red, suitable analogs and derivatives thereof, and the like. Suitable signal-generating enzymes include, but are not limited to, alkaline phosphatase, peroxidase, and urease. Any of the aforementioned labels can be obtained commercially, such as from Sigma Chemical Co. ("Sigma," St. Louis, Mo.).

Typically, the nucleic acid probe is attached to the solid surface at either the 5' or the 3' end, in many cases it is attached at the 3' end. It is believed that the nucleotides at the 5' and 3' ends, particularly the end that attaches to the solid surface, will tend to be the most susceptible to nuclease digestion, even when an appropriate protecting template nucleic acid is base-paired with the nucleic acid probe. Accordingly, in many embodiments of the invention, these terminal nucleotides are joined together by nuclease resistant linkages, such as are described above. As described above, it is a first nucleotide sequence in a nucleic acid probe, which sequence can be only a part of the entire nucleotide sequence of the nucleic acid probe, that is assessed for high fidelity hybridization with the nucleic acid template. Thus, in some embodiments, the first nucleotide sequence is linked at its 3' or 5' end to nucleotides or polynucleotides linked by nuclease-resistant linkages. The majority of linkages between nucleotides of a first nucleotide sequence are labile to the relevant nuclease (i.e., that nuclease to be used in the assay) to assure that sufficient cleavage-sites needed to allow the assay to discriminate between good hybridizations and poor hybridizations are present in the nucleic acid probe.

The assay can further comprise after the nucleic acid probe has been hybridized with the nucleic acid template and the nucleic acid probe has been attached to the solid surface, washing the solid surface with a suitable wash fluid, thereby removing unhybridized nucleic acid template. Such wash fluids are set forth in Ausubel et al. and Sambrook et al. and typically include a buffer for maintaining about a neutral pH, such as Tris or phosphate, a chelator, such as EDTA, salt such as about 0.15 M NaCl, and detergent, such as sodium dodecyl sulfate ("SDS").

Note that after the nuclease treatment, in many cases the solid surfaces can be rigorously washed since there no longer is a need to maintain hybridization with the nucleic acid template. However, prior to such washing it is important to render inactive the nuclease. For S1 nuclease, for example, ethylenediaminetetraacetic acid ("EDTA") and excess RNA such as tRNA can be used to stop the activity of the nuclease. For ribonuclease A, for example, a denaturing detergent such as SDS and a denaturation resistant protease such as proteinase K can be added to stop the activity of the nuclease. Other stop procedures are known in the art for other nucleases. Also, where the nucleic acid probe is attached through a binding pair, the wash conditions should preserve the binding pair interaction.

In many cases, it is desirable to fragment the nucleic acid template to create shorter fragments that more readily hybridize. Such fragmentation can for instance be carried out by shearing or, in the case of DNA, by treatment with a restriction enzyme having a specificity that generates average fragments of the desired size.

Examples of suitable nucleases for use with the invention have been recited above. It should be noted, however, that exonucleases such as exonuclease VII are generally used to supplement the nuclease activity of an endonuclease. If an exonuclease is used alone, validating experiments should be conducted to confirm that it sufficiently removes imperfectly hybridized first nucleotide sequences. Sources for nucleases include Sigma Chemical Co. (St. Louis, Mo.) for mung bean nuclease, micrococcal nuclease, nuclease P1, S1 nuclease, ribonuclease A and ribonuclease T1, BRL GIBCO (Grand Island, N.Y.) for exonuclease VII, mung bean nuclease, ribonuclease T1 and S1 nuclease, Promega Corp. (Madison, Wis.) for mung bean nuclease, nuclease BAL 31 and S1 nuclease, and Worthington Biochemical Corp. (Freehold, N.J.) for micrococcal nuclease.

It should be understood that the assay of the invention is not only useful to determine whether a nucleic acid sequence is present in a sample, but also to indicate the amount of such sequence present. Titration assays using several distinct solid surfaces and "standard" curves using known amounts of the nucleic acid of interest can be used to more carefully quantitate the amount of the nucleic acid of interest present in the sample.

Where methodologies are referred to herein without specific enumeration of now well-known method steps, generally, the following texts can be referenced for further details: Ausubel et al., *Short Protocols in Molecular Biology;* Ausubel et al., *Current Protocols in Molecular Biology;* Sambrook et al., *DNA Cloning, A Laboratory Manual;* and ≠Molecular Biology Protocols," web-site: listeria.nwfsc.noaa.gov/protocols.html.

In one embodiment of the invention, the sequence of the nucleic acid probe, or the array of nucleic acid probes, is derived from expressed sequence tags ("ESTs"), which are cDNA fragments of mRNAs expressed in a particular tissue.

The detection used in conjunction with the invention will depend on the nature of the label. Where a calorimetric or fluorescent label is used visual inspection or an optical instrument such as the fluorescence microscope from Olympus (Lake Success, N.Y.), the Plate Reader device from BioTek Instruments (Winooski, Vt.) and the CCD (charge-coupled device) camera from Princeton Instruments (Princeton, N.J.). Where radioisotopes are used, detection can comprise such spatially sensitive detection devices as the Phosphor Imager device (Molecular Dynamics, Sunnyvale, Calif.), or can comprise separately detecting individual solid surfaces in a detection apparatus such as a gamma-counter or a liquid scintillation counter.

Binding pairs are used in the invention in two ways. First, they are used to attach a nucleic acid probe to a solid surface, either before or after the hybridization step of the assay. Second, they can serve as the label of a nucleic acid probe by binding a detectable moiety after the nuclease contacting step of the assay. A prototypical binding pair is avidin-biotin, which two entities bind with extremely high affinity. One member of the binding pair can be attached to the nucleic acid probe, while the other is attached either to the solid surface or the detectable moiety. This attachment is typically covalent. The antibody-antigen binding pair is any suitable one, meaning that the pair exhibits sufficient affinity between the two components that the binding will hold throughout the detection method. Such antibody-antigen combinations include, but are not limited to, such combinations where the antigen is a hapten, a lectin, an immunoglobulin, or any antigenic material for which a sufficiently binding antibody exists or can be generated. Such combinations include those provided commercially by Sigma Chemical Company (St. Louis, Mo.).

The assay of the invention can be conducted in a closed reaction device such as that described in Southgate et al., "Parallel Reaction Cassette and Associated Devices," U.S. patent application Ser. No. 60/010,513 filed Jan. 24, 1996, Attorney Docket No. 11895. Additionally, the pumping, valves, storage devices, temperature control devices and detection devices described in this application can be usefully employed in the present invention. This Southgate et al. application is incorporated by reference into this disclosure in its entirety.

The temperature control device of the apparatus of the invention typically can maintain a temperature from about 4° C. to about 100° C., preferably from about 20° C. to about 65° C. The rotation device is typically a mechanical device driven by an electronic motor, preferably a stepper motor for which the rate of rotation can be closely controlled by an electronic controller. The use of the cylinder, with rotation, allows for the reaction volumes to be minimized.

It should noted that in the sequencing embodiment of the invention preferably all of the binding combinations are used. Alternatively, a subset of the combinations is used or some bases are substituted with alternate bases such as inosine having a broader base-pairing specificity than adenosine, thymidine, guanosine or cytosine. A subset will still provide substantial or, in some cases, complete sequence information, Statistical analysis can be used to determine the number of first nucleotide sequences needed to generate a useful probability of sufficient identifying overlaps that allow the nucleic acid segment in question to be partially or fully sequenced. It should be noted that by using all combinations, an abundance of overlaps will be identified. The sequencing method will encounter difficulty in sequencing regions of strict repetitive sequence, but other information, such as the length of the sample polynucleotide, should identify when such difficulties have been encountered. In some embodiments, first nucleotide sequences with lower hybridization melting temperatures are excluded from the array.

Figure 1:
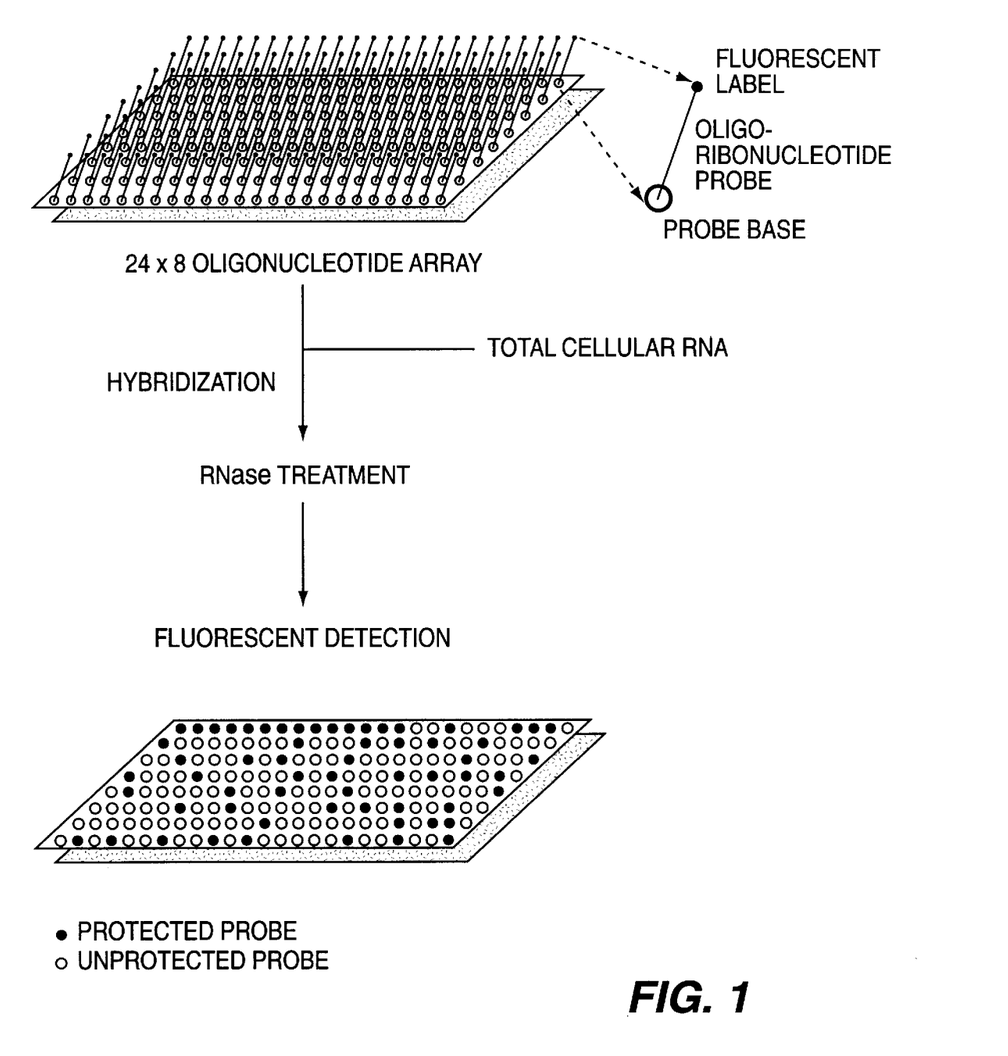
FIG. 1 shows a schematic representation of the assay.

In FIG. 1, a 24×8 array of solid surfaces is illustrated, together with an indication of the process steps required and the results obtained.

Figure 2A:
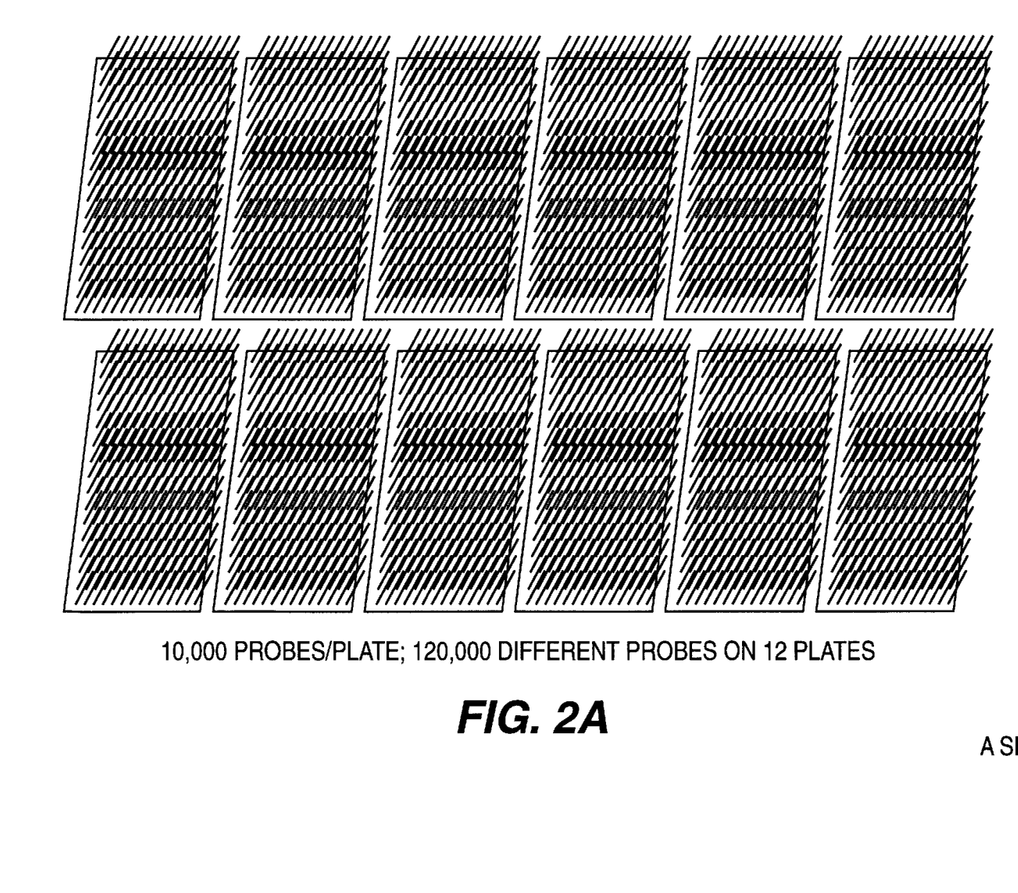
FIGS. 2A and 2B illustrate how a cylinder can be formed of a number of plates having solid surfaces with attached nucleic acid probes.
Figure 2B:
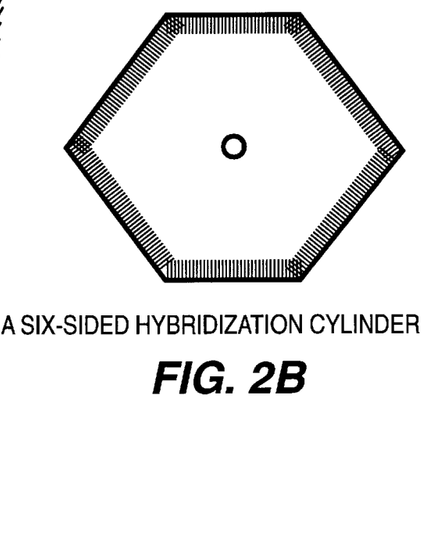

In FIG. 2A, a collection of 12 plates, each having 10,000 solid surfaces with nucleic acid probe bound thereto is illustrated. FIG. 2B shows 6 of these plates linked together to form a cylinder that can conveniently be rotated through the various solutions required for the assay.

As was noted at the outset of the present specification, it is contemplated that one context in which the assays set forth herein are preferably used is in a microfluidics device that is designed specifically for moving small volumes of fluids through fluid exchange channels that connect various sorts of fluid chambers. In particular, such a device comprises a fluid chamber, which is a generic term that describes chambers designed for storage of fluid reagents or reactants, i.e., a supply chamber, for locating reactants undergoing a reaction, i.e., a reaction chamber, for measuring a volume of a fluid, i.e., a metering chamber, and more. More particularly, the inventive device includes a reaction chamber wherein, for example, appropriate reagents are employed for hybridizing nucleic acid and digesting with a nuclease any single stranded nucleic acid remaining after the hybridization. The reaction chamber is comprised of any suitable material, as are all fluid chambers, such as, for example, glass, plastic, ceramic, or combinations thereof, and is connected to at least two fluid exchange channels for passaging material in and out of the reaction chamber. The reaction chamber preferably remains at a constant temperature of within about two degrees centigrade, wherein the temperature is preferably between about 20° C. and 65° C., and alternatively can have adjustable temperatures as in accordance with the requisites of the reactions to take place therein. The reaction chamber can also be the site at which the detection methods described hereinabove take place. Preferably, the solid surface of the described method when the inventive method is employed in the context of a microfluidics device is a microparticle, more preferably a paramagnetic microparticle.

The following examples further illustrate the present invention but, of course, should not be construed as in any way limiting its scope.

EXAMPLE 1

Solution Hybridization, Surface Attachment, and Nuclease Protection

The following oligonucleotides were utilized:

mActin-1: 5'-Fluorescein-TGTGGATCAGCAAGCAG-GAGTACGATGAGT-Biotin containing SEQ ID no: 1 mActin-5: 5'-TGTGGATCAGCAAGCAGGAGTACG-ATGAGT SEQ ID no: 1 mActin-2: 3'-ACACCTAGTCGTTCGTCCTCATG-CTACTCA SEQ ID no: 2

The wells of a polystyrene 96-well plate were coated with streptavidin (Sigma Biochemicals, St. Louis, Mo.) by incubating a 100 µ/ml solution of streptavidin in the wells overnight at room temperature. After removal of the streptavidin solution, the well surfaces were blocked by incubating them under 50 µl of 1 % bovine serum albumin, for 4 hours at room temperature. Hybridization reactions were conducted by reacting either 0.1 nmols of both mActin-1 and mActin-2, or 0.1 nmols of mActin-1 alone in 125 µl of 5X SSPE, 1 % SDS [5X SSPE: 0.9 mM NaCl, 50 mM NaH$_2$PO$_4$, pH 7.4, 50 mM EDTA]. The hybridization reaction mixtures were heated to 65° C. for 5 minutes and incubated at 37° C. for 2 hours. After hybridization, the reaction mixtures were transferred to separate wells on the 96-well plate and incubated at room temperature for 10 minutes. The wells were then aspirated and rinsed twice with 100 mM Tris, pH 7.5, 150 mM NaCl. 50 µl of 30 mM sodium acetate, pH 5, 50 mM NaCl and 1 mM ZnSO$_4$ was added to each well, mung bean nuclease (Boehringer Mannheim, Indianapolis, Ind.) was added as indicated in the table below and the reaction mixture was incubated at 37° C. for one hour. The presence of fluorescein-labelled oligonucleotide was detected with a fluorescein-peroxidase conjugate (Boehringer Mannheim, Indianapolis, Ind.) developed with 2,2'-azino-di-[3-ethylthiazoline sulfate ("ABTS") substrate (Boehringer Mannheim, Indianapolis, Ind.).

| Nuclease Concentration | Oligonucleotides | Result |
|---|---|---|
| 0 | none | + |
| 1.0 U/µl | mActin-1 + mActin-2 | +++ |
| 0.5 U/µl | mActin-1 + mActin-2 | +++ |
| 0 | mActin-1 + mActin-2 | ++++ |
| 0 | none | + |
| 1.0 U/µl | mActin-1 | + |
| 0.5 U/µl | mActin-1 | +++ |
| 0 | mActin-1 | ++++ |

EXAMPLE 2

Solution Hybridization, Surface Attachment, and Nuclease Protection

The methodology of Example 1 was repeated except that the nuclease was S1 nuclease (Promega, Madison, Wis.) the buffer used in the nuclease digestion step was 30 mM sodium acetate, pH 4.5, 50 mM NaCl, 1 mM zinc sulfate, 5% glycerol, and the nuclease digestion was conducted at room temperature for 30 minutes.

| Nuclease Concentration | Oligonucleotides [mActin-1 at .5 µM; mActin-2 & mActin-5 at 25 µM] | Result |
|---|---|---|
| 0 | none | − |
| 0 | mActin-2 | − |
| 1.0 U/µl | mActin-1 + mActin-2 | + |
| 0.5 U/µl | mActin-1 + mActin-2 | +++ |
| 0.25 U/µl | mActin-1 + mActin-2 | ++++ |
| 0 | mActin-1 + mActin-2 | ++++ |
| 0 | none | − |
| 0 | mActin-5 | − |
| 1.0 U/µl | mActin-1 + mActin-5 | + |
| 0.5 U/µl | mActin-1 + mActin-5 | + |
| 0.25 U/µl | mActin-1 + mActin-5 | ++++ |
| 0 | mActin-1 + mActin-5 | ++++ |

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed is:

1. A nuclease protection assay comprising:
   (A) attaching a nucleic acid probe comprising a first nucleotide sequence to a solid surface area;
   (B) contacting the nucleic acid probe with a nucleic acid template under conditions that promote hybridization between complementary polynucleotides, forming a probe-template complex if the template includes a segment that is complementary to the probe;
   (C) contacting the probe-template complex with a nuclease effective to selectively cleave the nucleotide bonds of (1) the first nucleotide sequence when the first nucleotide sequence is single stranded or (2) mismatched regions of the first nucleotide sequence when the first nucleotide sequence is in duplex nucleic acid; and
   (D) detecting the presence of duplex nucleic acids formed by the probe and template nucleic acids by detecting the presence of the first nucleotide sequence.

2. The assay of claim 1, wherein the attaching step occurs prior to the first contacting step.

3. The assay of claim 1, wherein the probe is attached to the solid surface area subsequent to hybridization between the probe and a template DNA.

4. The assay of claim 1, wherein the nucleic acid probe comprises one or more dinucleotides whose intranucleotide linkages are resistant to the said nuclease or wherein the nucleic acid probe is attached to the solid surface area by a linkage that is resistant to the said nuclease.

5. The assay of claim 4, wherein the one or more nuclease resistant linkages are located at or proximate to one or both of the termini of the probe.

6. The assay of claim 5, wherein nuclease resistant linkages are located at a terminus of the probe that is attached to the solid surface area.

7. The assay of claim 4, wherein the nucleic acid probe has a linker tail at one end.

8. The assay of claim 7, wherein the linker tail comprises a second nucleotide sequence that is not required to participate in the hybridization reaction and that is resistant to digestion by the nuclease whether or not it is hybridized with another polynucleotide.

9. The assay of claim 1, wherein the nucleic acid probe comprises a label, wherein the label is releasable from the nucleic acid probe when any nucleotide bond of the first nucleotide sequence is cleaved.

10. The assay of claim 9, wherein the label is attached to a nucleotide of the nucleic acid probe that is linked to another nucleotide of the nucleic acid probe by a nuclease resistant linkage.

11. The assay of claim 1, wherein the nucleic acid probe comprises a member of a binding pair.

12. The assay of claim 11, wherein the member of the binding pair is one of (a) the biotin/streptavidin binding pair, (b) an antigen/antibody specific for the antigen binding pair, (c) the amine/hydrazine moiety binding pair, or (d) the Protein A/immunoglobulinG binding pair.

13. The assay of claim 11, wherein the member of the binding pair is attached to a nucleotide of the nucleic acid probe that is linked to another nucleotide of the nucleic acid probe by a nuclease resistant linkage.

14. The assay of claim 11, wherein the attaching step comprises, after the first contacting step, contacting the nucleic acid probe with the solid surface area, wherein the other member of the binding pair is bonded to the solid surface area.

15. The assay of claim 1 wherein on a first solid surface area a first nucleic acid probe is attached and on a second solid surface area a second nucleic acid probe is attached, wherein the first and second solid surface areas are both processed through the assay steps, wherein the first nucleic acid probe and the second nucleic acid probe comprise a first label and a second label, respectively, which may be the same or different, wherein each label is releasable from its nucleic acid probe when any nucleotide bond of its first nucleotide sequence is cleaved, wherein the amount of first label differs from the amount of second label, and wherein the amount of label is approximately in inverse proportion to the anticipated frequency of the template polynucleotide that binds to the respective first or second nucleic acid probe.

16. The assay of claim 1 used for the identification or quantitation of an expressed mRNA, wherein the nucleic acid probe comprises at its 3' end a polyT segment and the first polynucleotide sequence comprises at least about 10 nucleotides distinct from the polyT segment, wherein the polyT-containing nucleic acid probe is complementary to the mRNA.

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

TGTGGATCAG    CAAGCAGGAG    TACGATGAGT    30

( 2 ) INFORMATION FOR SEQ ID NO:2:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:2:

ACACCTAGTC GTTCGTCCTC ATGCTACTCA  30

---

17. A method for the sequencing of a sample polynucleotide, the method comprising:
(A) preparing an array having a plurality of distinct nucleic acid probes, each of known nucleotide sequence, each comprising a first polynucleotide sequence, and each immobilized at an identifiable area on a solid surface, wherein each immobilized nucleic acid probe comprises a label attached to the nucleic acid probe, wherein the label is releasable from the nucleic acid probe when any nucleotide bond of the first polynucleotide sequence of the attached nucleic acid probe is cleaved;
(B) contacting the array with the sample polynucleotide or fragments thereof under conditions that promote hybridization between complementary nucleic acids;
(C) contacting the solid surface areas of the array with a nuclease effective to selectively cleave the nucleotide bonds of (1) the first polynucleotide sequence when the first polynucleotide sequence is single stranded or (2) mismatched regions of the first polynucleotide sequence when the first polynucleotide sequence is in duplex nucleic acid;
(D) removing released label from the solid surface; and
(E) detecting any label remaining on the solid surface areas and identifying the nucleic acid probe immobilized at the solid surface areas where label is detected.

18. The method of claim 17, further comprising
(F) compiling the identities of the nucleic acid probes that were protected from nuclease digestion in step (C) hereof; and
(G) aligning the first polynucleotide sequences of the compiled nucleic acid probes by identifying sequence overlaps between the first polynucleotide sequences of the compiled nucleic acid probes.

19. The method of claim 17, wherein the first polynucleotide sequence is an 8-mer and the array comprises first polynucleotide sequences for each of the 65,536 possible such sequences or multiple arrays are processed which together comprise first polynucleotide sequences for each of the 65,536 possible such sequences.

* * * * *